United States Patent
Shimamoto

(10) Patent No.: US 6,861,505 B1
(45) Date of Patent: Mar. 1, 2005

(54) METHOD FOR RECOVERING SOLUBLE PROTEIN

(75) Inventor: Nobuo Shimamoto, Mishima (JP)

(73) Assignee: HSP Research Institute, Inc., Osaka (JP)

( * ) Notice: Subject to any disclaimer, the term of this patent is extended or adjusted under 35 U.S.C. 154(b) by 0 days.

(21) Appl. No.: 09/701,005

(22) PCT Filed: May 17, 1999

(86) PCT No.: PCT/JP99/02574
§ 371 (c)(1),
(2), (4) Date: Nov. 22, 2000

(87) PCT Pub. No.: WO99/61649
PCT Pub. Date: Dec. 2, 1999

(30) Foreign Application Priority Data

May 26, 1998 (JP) ............................................ 10-144758

(51) Int. Cl.⁷ .............................. C07K 1/14; C07K 1/30
(52) U.S. Cl. ........................ 530/344; 530/422; 530/424
(58) Field of Search ................................ 530/344, 422, 530/424

(56) References Cited

FOREIGN PATENT DOCUMENTS

| | | |
|---|---|---|
| EP | 0360937 | 4/1990 |
| JP | A59500597 | 4/1984 |
| JP | A1168298 | 7/1989 |
| JP | 1-168298 * | 7/1989 |
| JP | A5502888 | 5/1993 |
| WO | A1-8303103 | 9/1983 |
| WO | A1-9200993 | 1/1992 |

OTHER PUBLICATIONS

Database Chemabs 'Online!, Chemical Abstracts Service, Columbus, Ohio, USA, Shimamoto, et al, "Efficient Solubilization Of Proteins Overproduced As Inclusion Bodies By Use Of An Extreme Concentration Of Glycerol", retrieved from STN, Database accession no. 130:232959 HCA, XP–002173883, Abstract, &Tech. Tips Online (1998).

* cited by examiner

Primary Examiner—Brenda Brumback
Assistant Examiner—Anish Gupta
(74) Attorney, Agent, or Firm—Birch, Stewart, Kolasch & Birch, LLP

(57) ABSTRACT

The present invention relates in providing a process for recovering a soluble protein having a higher recovery rate by suppressing the aggregation of the protein when a denaturing agent is removed from the solubilization treatment solution containing a solubilized protein; and providing a process for removing a denaturing agent from the above solubilization treatment solution in which the aggregation of the protein is suppressed. In a process for recovering a soluble protein comprising the steps of removing a denaturing agent from a solubilization treatment solution prepared by solubilizing insoluble protein aggregates using the denaturing agent, the process of the present invention is characterized by subjecting the solubilization treatment solution to a treatment of removing the denaturing agent in the presence of a dihydric to tetrahydric, polyhydric alcohol at a concentration of 60 to 99% by volume, and thereafter diluting with a diluent solution the treatment solution obtained after the removal treatment. In a process for removing a denaturing agent from a solubilization treatment solution prepared by solubilizing insoluble protein aggregates using the denaturing agent, the process of the present invention is characterized by subjecting the solubilization treatment solution to a treatment of removing the denaturing agent in the presence of a dihydric to tetrahydric, polyhydric alcohol.

14 Claims, No Drawings

METHOD FOR RECOVERING SOLUBLE PROTEIN

This application is the national phase under 35 U.S.C. § 371 of PCT International Application No. PCT/JP99/02574 which has an International filing date of May 17, 1999, which designated the United States of America.

TECHNICAL FIELD

The present invention relates to a process for recovering a soluble protein in which a high recovery rate can be achieved. Further, the present invention relates to a process for removing a denaturing agent in which a recovery rate of the protein is high.

BACKGROUND ART

When heterologous genes are expressed in large amounts in bacteria or the like by means of recombinant DNA techniques, the produced protein may be obtained in an insoluble form (inclusion bodies). In addition, when a protein is chemically modified, there may be some cases where aggregation also takes place between the proteins, to form insoluble aggregates. When a protein is purified from the protein in an insoluble form, there is generally employed a process comprising the steps of once solubilizing inclusion bodies or aggregates by using a denaturing agent, and thereafter removing the denaturing agent by dialysis to give a protein solution.

However, in the process described above, a major part of the desired protein has been subjected to re-aggregation during dialysis to form insoluble aggregates. Since the formation of aggregates during the dialysis as described above can be a factor for lowering a recovery rate of a soluble protein, a process for suppressing aggregation of the protein has been desired.

Accordingly, a first object of the present invention is to provide a process for recovering a soluble protein having a higher recovery rate by suppressing the aggregation of the protein when a denaturing agent is removed from the solubilization treatment solution containing a solubilized protein. Further, a second object of the present invention is to provide a process for removing a denaturing agent from the above solubilization treatment solution in which the aggregation of the protein is suppressed. These objects and other objects of the present invention will be apparent from the following description.

DISCLOSURE OF INVENTION

Specifically, the present invention relates to:

[1] in a process for recovering a soluble protein comprising the steps of removing a denaturing agent from a solubilization treatment solution prepared by solubilizing insoluble protein aggregates using the denaturing agent, the process characterized by subjecting the solubilization treatment solution to a treatment of removing the denaturing agent in the presence of a dihydric to tetrahydric, polyhydric alcohol at a concentration of 60 to 99% by volume, and thereafter diluting with a diluent solution the treatment solution obtained after the removal treatment; and

[2] in a process for removing a denaturing agent from a solubilization treatment solution prepared by solubilizing insoluble protein aggregates using the denaturing agent, the process being characterized by subjecting the solubilization treatment solution to a treatment of removing the denaturing agent in the presence of a dihydric to tetrahydric, polyhydric alcohol at a concentration of 60 to 99% by volume.

BEST MODE FOR CARRYING OUT THE INVENTION

The term "insoluble protein aggregates" to be solubilized in the present invention refers to, for instance, inclusion bodies of intact proteins, proteins obtainable by gene manipulations, chemically modified proteins, or the like, and aggregates obtained by aggregating such proteins.

In addition, as the denaturing agent usable in the present invention, there can be used known denaturing agents which have been conventionally used for the solubilization of the proteins without limitation. The denaturing agent includes, for instance, chaotropic reagents such as guanidine hydrochloride and urea. The concentration of the denaturing agent may be at a level that the insoluble protein aggregates can be solubilized.

A known process using a denaturing agent or the like can be employed for the solubilization of the insoluble protein aggregates. By the solubilization procedures there is obtained a solubilization treatment solution comprising the denaturing agent and a protein which is denatured and solubilized by the denaturing agent.

The protein concentration of the solubilization treatment solution is not particularly limited. From the viewpoints of suppressing the formation of precipitates in the subsequent removal process of the denaturing agent and dilution process and keeping the stability of the protein, the protein concentration is preferably 0.1 mg/mL or more, more preferably 2 mg/mL or more. In addition, the protein concentration is preferably 200 mg/mL or less, more preferably 20 mg/mL or less.

Before the solubilization of the insoluble protein aggregates, the insoluble protein aggregates to be solubilized may be washed with a buffer containing a surfactant having a characteristic that does not cause the protein to denature, such as Tween™ 20, Triton™ X-100, NP40, and deoxycholate, or the like.

In the present invention, the treatment of removing the denaturing agent from the solubilization treatment solution is carried out in the presence of a dihydric to tetrahydric, polyhydric alcohol.

The process for removing the denaturing agent from the solubilization treatment solution is not particularly limited. The process includes a dialysis process for dialyzing the treatment solution against a solution containing a dihydric to tetrahydric, polyhydric alcohol; a process for removing the denaturing agent using a fractionated membrane or the like with adding a solution containing a dihydric to tetrahydric, polyhydric alcohol to the treatment solution, or the like. When the present invention is carried out in a small scale, the dialysis process is convenient.

When the dialysis process is carried out, from the viewpoint of suppressing the formation of the precipitates during dialysis as much as possible, it is more preferable that the dialysis is carried out after an equal volume of a dihydric to tetrahydric, polyhydric alcohol is previously added to the solubilization treatment solution.

The concentration of the polyhydric alcohol in the solution containing a dihydric to tetrahydric, polyhydric alcohol is preferably 60% by volume or more, more preferably 70% by volume or more, from the viewpoints of suppressing the amount of the formed precipitates caused by aggregation of the protein during the treatment of removing the denaturing agent, and improving the recovery rate of the soluble protein. In addition, the concentration of the polyhydric alcohol is preferably 99% by volume or less, more preferably 90% by volume or less, from the viewpoints of suppressing the aggregation of the protein after the treatment of removing the denaturing agent and keeping the stability of the protein.

The pH of the solution containing a dihydric to tetrahydric, polyhydric alcohol is not particularly limited. For instance, the pH in the range of 3 to 9 is preferable. In addition, the temperature of the solution containing the polyhydric alcohol during the removal treatment is preferable in the range of −5° to 200° C., from the viewpoint of suppressing the denaturation of the protein. In addition, in the solution containing a dihydric to tetrahydric, polyhydric alcohol, there may be contained other components such as a buffer, a surfactant, a chelating agent, a reducing agent, and a salt.

The dihydric to tetrahydric, polyhydric alcohol includes, for instance, ethylene glycol, propylene glycol, glycerol, butylene glycol, erythritol, and the like. Among them, glycerol is preferable. These polyhydric alcohols may be used alone or in admixture of two or more kinds.

As described above, the protein is recovered in a state that the denaturing agent is removed to dissolve the protein in the solution containing a dihydric to tetrahydric, polyhydric alcohol. The recovered protein can be stored without any treatments at a low temperature at 0° C. or less in a freezing or non-freezing state with a freezer or the like. Therefore, one embodiment of the present invention is to provide a process for removing a denaturing agent by carrying out a treatment of removing the denaturing agent in the presence of a dihydric to tetrahydric, polyhydric alcohol.

A further embodiment of the present invention is to provide a process for recovering a soluble protein, the process comprising subsequently diluting with a diluent solution a treatment solution after the removal treatment obtained in the manner described above. The diluent solution is not particularly limited. For example, there can be included as preferable ones known buffers such as Tris-hydrochloric acid buffer and phosphate buffer.

The extent of dilution may be such that the treatment solution after the removal treatment is diluted using a diluent solution of preferably 3 times by volume or more of the treatment solution after the removal treatment, more preferably 5 times by volume or more, from the viewpoints of suppressing the formation of aggregates and making a concentration of the dihydric to tetrahydric, polyhydric alcohol in a desired concentration. The extent of dilution may be such that the treatment solution after the removal treatment is diluted using a diluent solution of preferably 100 times by volume or less of the treatment solution after the removal treatment, more preferably 20 times by volume or less, from the viewpoints of obtaining the stability and the solution having a protein concentration in a range so as not to impair the subsequent procedures such as purification process. By the dilution described above, there can be obtained a solution of which concentration of the dihydric to tetrahydric, polyhydric alcohol is 0.5 to 30% by volume or so.

An embodiment for the dilution procedures is not particularly limited. However, in the case where the dilution is carried out, it is more preferable to dilute the solution in as a short period of time as possible, for instance, within several minutes as a period of time required for dilution, for the purpose of suppressing the formation of aggregates. In order to dilute the solution in a shorter period of time, there may be preferably carried out procedures, for instance, a procedure of mixing the solution with adding a treatment solution after the removal treatment to a diluent solution.

As described above, the soluble protein is recovered in the state in which the soluble protein is dissolved in the solution containing a dihydric to tetrahydric, polyhydric alcohol. The recovered protein can be stored at a low temperature of 0° C. or less in the freezing state or non-freezing state directly with a freezer or the like. According to the process of the present invention, since the amount of precipitates formed containing the protein can be remarkably suppressed, the precipitates being formed in the course of the treatment of removing a denaturing agent, the recovery rate of the soluble protein can be notably improved, as compared to the conventional process.

The soluble protein recovered by the process of the present invention is incorporated as a sample for a known purification process, whereby a protein can be obtained in a higher yield.

Next, the present invention is described in further detail on the basis of the working examples, without intending to limit the present invention to these examples.

EXAMPLES 1 TO 6

Six kinds of proteins were recovered as soluble proteins. As to Examples 1 to 5, each sample was obtained in the form of inclusion bodies by incorporating a nucleotide carrying a given nucleotide sequence into an expression vector, and expressing a desired protein in a host in a large amount. In addition, as to Example 6, the sample was obtained by labeling chicken egg-derived avidin with fluorescein isothiocyanate (FITC) and forming aggregates thereof. The proteins in Examples 1 to 5 are as follows.

Example 1: Sigma factor $\sigma^{70}$ mutants resulting from deletion of 130th to 374th amino acids and four derivatives thereof (derived from *E. coli*)

Example 2: TFIIH Homolog comprising 175 amino acid residues resulting from fusion of glutathione-S-transferase (GST) at N-terminal (derived from *Drosophila melanogaster*)

Example 3: Chloroplast sigma factor Sig A with transit peptide (derived from *Arabidopsis thaliana*)

Example 4: Chloroplast sigma factor Sig A without transit peptide (derived from *Arabidopsis thaliana*)

Example 5: Translation factor resulting from binding histidine 6 residues at C-terminal (derived from *Tetrahymena thermophila*).

A sample of inclusion bodies or aggregates prepared as described above was washed twice with 10 mM Tris-hydrochloric acid buffer (pH 7.5) containing a surfactant shown in Table 1 using a homogenizer. The concentrations and the kinds of surfactants as used herein are as follows. Tx: 0.5% by weight Triton™ X-100; D: 2% by weight deoxycholate; Tw: 0.05% by weight Tween™20. During washing, each of the samples was not dissolved, but obtained as a suspension.

The washed sample was dissolved in 10 mM Tris-hydrochloric acid buffer (pH 7.5) containing 6 M guanidine hydrochloride, to give a solubilization treatment solution. The protein concentration at this stage was determined by BCA protein assay (Pierce). As a result, the protein concentration was in the range of 2 to 20 mg protein/mL.

The resulting solubilization treatment solution was transferred into Eppendorf tubes, and centrifuged at 4° C. and at 13000 rpm for 20 minutes. Supernatant was transferred into a 8/32 or 20/32 dialysis tube, and an equal volume of glycerol was added thereto. A solution prepared by mixing glycerol and TEM buffer [comprising 10 mM Tris-hydrochloric acid (pH 7.5), 1 mM EDTA, and 1 mM 2-mercaptoethanol] at a volume ratio of 3:1 was used as a dialysate, and the solubilization treatment solution was dialyzed against dialysate. The dialysate was stirred at 4° C. and at a rotational speed of 10 rpm. The dialysate was exchanged with a fresh solution twice every two to four hours, or once at eighth hour. After the termination of dialysis, the dialyzed solution (a treatment solution after the removal treatment) was stored in a freezer.

The treatment solution after the treatment of removing a denaturing agent obtained as described above, the treatment solution having a protein concentration of 1 to 10 mg/mL, was diluted by adding dropwise TEM buffer containing 0.1 M sodium chloride as a diluent solution, to give a protein solution of which glycerol concentration was 5% by volume. The amount of the diluent solution was 14 times by volume that of the treatment solution after the treatment of removing a denaturing agent. The resulting soluble protein solution was placed on ice, and thereafter centrifuged at 10000×g or more to remove the precipitates. In order to clarify the extent which could be recovered as a soluble protein with regard to the soluble protein solution obtained as described above, the solubilization rate of each protein was determined.

The solubilization rate of the protein was obtained as follows.

The soluble protein solution, the treatment solution after the treatment of removing a denaturing agent (75% by volume glycerol solution) and the solubilization treatment solution (6 M guanidine hydrochloride solution) for inclusion bodies or aggregates were respectively analyzed by SDS-PAGE. The gel after electrophoresis was reversely stained by the process described in *FEBS Lett.* 296, 300–304. Thereafter, the intensity of each band was compared with the band intensity of a standard protein (75% by volume glycerol-containing solution) at various concentrations to quantify the amount of the protein for each sample. The ratio of the amount of the protein in the soluble protein solution to the amount of the protein in the solubilization treatment solution of inclusion bodies or aggregates was obtained and defined as a solubilization rate.

The extents of improvement in the solublization rate as compared with the conventional process were shown by the solubilization rate (A) for the soluble protein in the soluble protein solution obtained by the process of the present invention, and by the solubilization rate (B) for the soluble protein in the protein solution obtained by the following conventional process (control experiment).

The control experiment was carried out as follows.

A solubilization treatment solution of inclusion bodies or aggregates obtained in the same manner as in Examples was prepared. This solution was transferred into Eppendorf tubes, and centrifuged at 4° C. and 13000 rpm for 20 minutes. Supernatant was dialyzed against TEM buffer containing 0.1 M sodium chloride, the TEM buffer having glycerol concentration of 5% by volume. Subsequently, the dialyzed solution was centrifuged. The solubilization rate for the soluble protein in the resulting supernatant was obtained.

The results are shown in Table 1.

TABLE 1

| Examples | Vector Used/Host | Surfactant During Washing | Solubilization Rate (A) (%) | Ratio of Solubilization % (A) to Solubilization % (B) (-fold) |
|---|---|---|---|---|
| 1 | pGEMD/ E. coli BL21 (DE3) | Tx | 100 | 10 |
| 2 | pGET-4T-2/ E. coli BL21 (DE3) | Tx | 9 | 180 |
| 3 | pET15b/ E. coli BL21 (DE3, pLysS) | D | 60 | 85 |
| 4 | pET15b/ E. coli BL21 (DE3, pLysS) | D | 15 | 11 |
| 5 | pTE3/ E. coli BL21 (DE3) | Tw | 100 | 110 |
| 6 | —/— | — | 100 | 10 |

As shown in Table 1, according to the process of the present invention, the improvements in the solubilization rate of the protein could be achieved to a level of 10 to 180-folds that of the conventional process, so that a soluble protein could be remarkably efficiently recovered.

Equivalent

Those skilled in the art will recognize, or be able to ascertain using simple routine experimentation, many equivalents to the specific embodiments of the invention described in the present specification. Such equivalents are intended to be encompassed in the scope of the present invention as recited in the following claims.

INDUSTRIAL APPLICABILITY

According to the recovering process of the present invention, there is achieved a process for recovering a soluble protein in a high recovery rate. In addition, according to the process for removing a denaturing agent of the present invention, the denaturing agent can be removed with suppressing the aggregation of the protein.

What is claimed is:

1. A process for recovering a soluble protein from insoluble protein aggregates comprising:
  (a) solubilizing insoluble protein aggregates using a denaturing agent, to obtain a solubilization treatment solution,
  (b) treating the solubilization treatment solution with one or more polyhydric alcohols selected from the group consisting of dihydric alcohol, trihydric alcohol, and tetrahydric alcohol at a concentration of 60 to 99% by volume to remove the denaturing agent, thereby giving a removal treatment solution, and thereafter
  (c) diluting the removal treatment solution obtained in (b) with a diluent solution.

2. The process according to claim 1, wherein said step (b) is carried out by dialyzing said solubilization treatment solution against a solution comprising said polyhydric alcohol.

3. The process according to claim 1 or 2, wherein in said step (c) the treatment solution is diluted using an amount of said diluent solution of 3 to 100-folds by volume of said treatment solution.

4. The process according to claim 1, wherein the diluent solution is a buffer.

5. The process according to claim 1, wherein the polyhydric alcohol is one or more kinds selected from the group consisting of ethylene glycol, propylene glycol, glycerol, butylene glycol, and erythritol.

6. A process for removing a denaturing agent from a solubilization treatment solution, wherein the solubilization treatment solution is prepared by solubilizing insoluble protein aggregates using the denaturing agent, comprising the step of treating said solubilization treatment solution with one or more polyhydric alcohols selected from the group consisting of dihydric alcohol, trihydric alcohol and tetrahydric alcohol at a concentration of 60 to 99% by volume.

7. The process according to claim 6, wherein said step is carried out by dialyzing the solubilization treatment solution against a solution containing said polyhydric alcohol.

8. The process according to claim 1, wherein the concentration of said polyhydric alcohol is 70 to 99% by volume.

9. The process according to claim 1, wherein the concentration of said polyhydric alcohol is 60 to 90% by volume.

10. The process according to claim 1, wherein the concentration of said polyhydric alcohol is 70 to 90% by volume.

11. The process according to claim 6, wherein the concentration of said polyhydric alcohol is 70 to 99% by volume.

12. The process according to claim 6, wherein the concentration of said polyhydric alcohol is 60 to 90% by volume.

13. The process according to claim 6, wherein the concentration of said polyhydric alcohol is 70 to 90% by volume.

14. A process for recovering a soluble protein from a solubilization treatment solution, wherein said solubilization treatment solution is prepared by solubilizing insoluble protein aggregates using a denaturing agent, comprising the steps of:

(1) treating the solubilization treatment solution with one or more polyhydric alcohols selected from the group consisting of dihydric alcohol, trihydric alcohol and tetrahydric alcohol at a concentration of 60 to 99% by volume to remove the denaturing agent, thereby giving a removal treatment solution, and (2) diluting the removal treatment solution obtained in step (1) with a diluent solution.

* * * * *